(12) United States Patent
Zoicas

(10) Patent No.: US 8,903,479 B2
(45) Date of Patent: Dec. 2, 2014

(54) REAL TIME QRS DURATION MEASUREMENT IN ELECTROCARDIOGRAM

(75) Inventor: Vasile Zoicas, La Gaude (FR)

(73) Assignee: Texas Instruments Incorporated, Dallas, TX (US)

(*) Notice: Subject to any disclaimer, the term of this patent is extended or adjusted under 35 U.S.C. 154(b) by 181 days.

(21) Appl. No.: 13/548,175

(22) Filed: Jul. 12, 2012

(65) Prior Publication Data
US 2013/0338518 A1 Dec. 19, 2013

(30) Foreign Application Priority Data

Jun. 19, 2012 (EP) .................................... 12290201

(51) Int. Cl.
*A61B 5/0468* (2006.01)
*A61B 5/0452* (2006.01)

(52) U.S. Cl.
USPC ........................................................ 600/516

(58) Field of Classification Search
CPC .... A61B 5/0002; A61B 5/0006; A61B 5/002; A61B 5/0022; A61B 5/04012; A61B 5/0404; A61B 5/0452; A61B 5/0456; A61B 5/0472
USPC .................. 600/509, 515, 516, 518, 521, 523
See application file for complete search history.

(56) References Cited

U.S. PATENT DOCUMENTS 4,492,235 A 1/1985 Sitrick
6,804,555 B2 10/2004 Warkentin
2005/0049515 A1* 3/2005 Misczynski et al. .......... 600/509
2007/0096927 A1* 5/2007 Albert ........................ 340/573.1
2008/0065162 A1 3/2008 Pittaro
2008/0194978 A1 8/2008 Beker et al.
2008/0300496 A1 12/2008 Lee et al.
2009/0048528 A1 2/2009 Hopenfeld et al.

FOREIGN PATENT DOCUMENTS

EP 2016894 1/2009
WO WO2011-115579 9/2011

OTHER PUBLICATIONS

"QRS complex", Wikipedia, pp. 1-5, available at http://en.wikipedia.org/wiki/QRS_complex on May 14, 2012.
"ADS1294, ADS1294R, ADS1296, ADS1296R, ADS1298, ADS1298R Low-Power, 8 Channel, 24-Bit Analog Front-End for Biopotential Measurements", Texas Instruments Incorporated, Jan. 2010, pp. 1-86.
Vasile Zoicas, "Real Time QRS Algorithm Based on Adaptive IIR Filtered Threshold", U.S. Appl. No. 13/434,725, filed Mar. 29, 2012, pp. 1-28.

(Continued)

Primary Examiner — Allen Porter, Jr.
(74) Attorney, Agent, or Firm — Alan A. R. Cooper; Frederick J. Telecky, Jr.

(57) ABSTRACT

ECG data may be processed in a mobile device by receiving a stream of filtered ECG data samples comprising PQRST pattern cycles. An R point of a PQRST pattern in the filtered ECG data is determined. A portion of samples is selected from the filtered ECG data surrounding the R point. QRS duration of the PQRST pattern is then determined by processing the selected portion of samples using an application program executed by the mobile device.

7 Claims, 12 Drawing Sheets

(56) References Cited

OTHER PUBLICATIONS

"A Wearable Smartphone-Based Platform for Real-Time Cardiovascular Disease Detection Via Electrocardiogram Processing", Joseph J. Oresko, et al., IEEE Transactions on Information Technology in Biomedicine, IEEE Service Center, Los Alamitos, CA, US, vol. 14, No. 3, May 1, 2010, pp. 734-740, XP011345714, ISSN: 1089-7771, DOI: 10.1109/TITB.2010.2047865.

"Correction of ECG Baseline Wander Application to the Pan & Tompkins QRS Detection Algorithm", Nehla Debbabi, et al., I/V Communications and Mobile Network (ISVC), 2010 5th International Symposium On, IEEE, Piscataway, NJ, USA, Sep. 30, 2010, pp. 1-4, XP031815598, ISBN: 978-14244-5996-4.

"Interpolation for Ambulatory ECG Measurements", A. Singh, et al., Nov. 9, 1989-Nov. 12, 1989, Nov. 11, 2009, pp. 1397-1398, XP010088422.

* cited by examiner

REAL TIME QRS DURATION MEASUREMENT IN ELECTROCARDIOGRAM

CLAIM OF PRIORITY UNDER 35 U.S.C. 119(A)

The present application claims priority to and incorporates by reference European Patent Application number EP12290201, filed Jun. 19, 2012, entitled "Real Time QRS Duration Measurement in Electrocardiogram".

FIELD

The embodiments of the invention generally relate to analysis of electrocardiogram signals, and in particular to the use of low cost consumer devices for this purpose.

BACKGROUND

Electrocardiography is a transthoracic (across the thorax or chest) interpretation of the electrical activity of the heart over a period of time, as detected by electrodes attached to the outer surface of the skin and recorded by a device external to the body. The recording produced by this noninvasive procedure is termed as electrocardiogram (also ECG or EKG). An electrocardiogram (ECG) is a test that records the electrical activity of the heart.

ECG is used to measure the rate and regularity of heartbeats as well as the size and position of the chambers, the presence of any damage to the heart, and the effects of drugs or devices used to regulate the heart, such as a pacemaker.

An ECG device detects and amplifies the tiny electrical changes on the skin that are caused when the heart muscle depolarizes during each heartbeat. At rest, each heart muscle cell has a negative charge (membrane potential) across its outer wall (or cell membrane). Increasing this negative charge towards zero (via an influx of the positive ions, Na+ and Ca++) is called depolarization, which activates the mechanisms in the cell that cause it to contract. During each heartbeat a healthy heart will have an orderly progression of a wave of depolarization that is triggered by the cells in the sinoatrial node, spreads out through the atrium, passes through "intrinsic conduction pathways" and then spreads all over the ventricles. This is detected as tiny rises and falls in the voltage between two electrodes placed either side of the heart which is displayed as a wavy line either on a screen or on paper. This display indicates the overall rhythm of the heart and weaknesses in different parts of the heart muscle.

Usually, more than two electrodes are used and they can be combined into a number of pairs, for example: Left arm (LA), right arm (RA), and left leg (LL) electrodes form the three pairs LA+RA, LA+LL, and RA+LL. The output from each pair is known as a lead. Each lead is said to look at the heart from a different angle. Different types of ECGs can be referred to by the number of leads that are recorded, for example 3-lead, 5-lead, or 12-lead ECGs (sometimes simply "a 12-lead"). A 12-lead ECG is one in which 12 different electrical signals are recorded at approximately the same time and will often be used as a one-off recording of an ECG, traditionally printed out as a paper copy. 3- and 5-lead ECGs tend to be monitored continuously and viewed only on the screen of an appropriate monitoring device, for example during an operation or while being transported in an ambulance. There may or may not be any permanent record of a 3- or 5-lead ECG, depending on the equipment used.

Several studies show that QRS duration above ~120 msec is a pathological sign and often correlated with various myocardial diseases. Measuring the duration of QRS complex (ventricular depolarization) in an accurate manner is a challenge, especially for a noisy ECG. Typically, clinicians measure the QRS duration manually on the printed paper ECG or on a monitor screen. Some clinicians use computer based software (SW) for such analysis but the software does not measure duration in real time; the ECG is first recorded and then is post-processed using a dedicated ECG analysis tool (e.g. MAC 1600 Marquette 12SL ECG analysis program from General Electric).

Another system for measuring QRS duration is invasive and intended for pacemakers. Another system uses high frequency components present in the QRS wave, but it does not operate in strict real time since it needs to average several beats.

There are generally two types of existing heart monitors: 1) fitness portable monitors having limited capabilities, such as only heart rate, but not ECG waveform, no pre-alert, and poor QRS detector performances; 2) medical grade monitors which are not really portables although they have good performances and provide pre-alerts. Cost of medical grade equipment such as ECG, EMG (electromyogram), EEG (electroencephalogram) is still prohibitive for consumers. Some existing solutions may have good performances but they are not real time. Some others are portable and real time but show poor performances, such as fitness Heart Rate monitors. Medical grade equipment has reasonable performance and generally operates in real time but they are not compact enough for use as portable equipment and are expensive.

BRIEF DESCRIPTION OF THE DRAWINGS

Particular embodiments in accordance with the invention will now be described, by way of example only, and with reference to the accompanying drawings.

Figure 1:
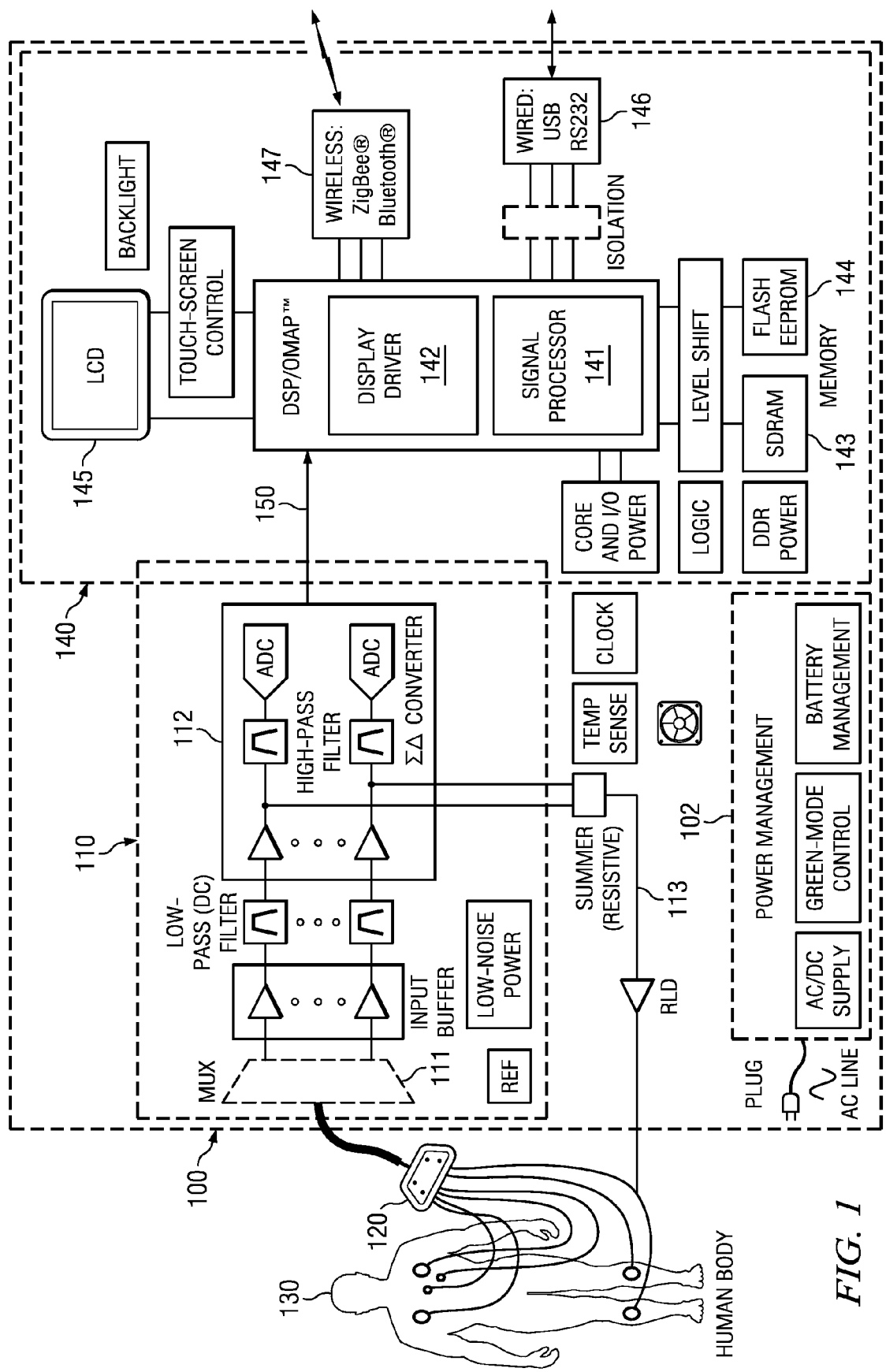
FIG. 1 is a block diagram illustrating an embodiment of the invention within a mobile ECG system.

Other features of the present embodiments will be apparent from the accompanying drawings and from the detailed description that follows.

DETAILED DESCRIPTION OF EMBODIMENTS

Specific embodiments of the invention will now be described in detail with reference to the accompanying figures. Like elements in the various figures are denoted by like reference numerals for consistency. In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

It has now been determined experimentally that there is a relationship between QRS duration and rising/falling inflexion points present on the QRS wave shape. Inflexion points may be detected using a first order derivative and a straight line equation may be used to intercept the x axis representing the baseline of a normalized QRS wave. QRS duration may then be calculated based on the x-axis crossings of the straight line equations for each QRS wave pattern. This makes the solution very robust to the noise; therefore no beat to beat average is needed. As a consequence, duration of every single beat may be accurately measured in real time.

Embodiments of the invention provide a system that accurately measures the QRS duration of every single heart beat in real time during ECG monitoring. Embodiments may operate well in a noisy environment and therefore may be used during ambulatory monitoring or during fitness activity for generating real time pre-alert. For example, an alert may be generated if QRS duration is higher than 120 msec for one or more heartbeats during an exercise sequence.

Embodiments provide very good QRS accuracy measurement with various type of ECG, both normal and abnormal PQRST shapes.

Embodiments may be easily encapsulated in a monitoring application using an open OS (operating system) application framework, for example.

Measurement of an ECG signal is challenging due to the presence of DC offset and various interference signals. This potential can be up to 300 mV for a typical electrode. The interference signals include the 50/60-Hz interference from the power supplies, motion artifacts due to patient movement, radio frequency interference from electro-surgery equipments, defibrillation pulses, pace maker pulses, other monitoring equipment, etc. Embodiments of the present invention allow real time processing and analysis of heart abnormalities with high detection performance, thereby enabling generation of real time pre-alerts in degraded conditions which may be caused by body motions, rubbing, or deformation of electrodes, fitness of the person being tested, etc., for example.

Embodiments may be provided in a low cost mobile health ECG monitoring device. For example, embodiments may be implemented within a smart phone handset, a personal data assistant (PDA), a tablet computer, notebook computer, personal computer, etc. These devices may be used for personal feedback and information and may also be linked via the cell network or other wireless network to support a consumer medical market for telemedicine. Other embodiments may be implemented in medical grade equipment for use in a doctor's office or hospital, for example.

An embodiment may receive and filter an ECG signal and perform QRS detection as described briefly herein and in more detail in U.S. patent application Ser. No. 13/434,725, entitled "Real Time QRS Algorithm Based on Adaptive IIR Filtered Threshold" which is incorporated by reference herein. This embodiment uses several cascaded filters that are coupled to an adaptive filtered threshold through an IIR (infinite impulse response) filter whose cutoff frequency is adapted in real time with logarithmic scaling to the noise level from the original signal. However, other embodiments of the invention may perform QRS duration measurement as described herein on ECG signals that are filtered and normalized using other known or later developed techniques.

FIG. 1 is a block diagram illustrating an embodiment of the invention within a mobile ECG system 100. An analog front end section 110 is coupled to a set of leads 120 that are coupled to a subject 130 that is being monitored. Monitored subject 130 is usually a human; however, embodiments of the invention may be used for monitoring other types of subjects such as animal, bird, or reptile, for example. Monitoring leads 120 comprise multiple leads that are attached to various points on subject 130. Typically, three, five, seven, or twelve leads are used for ECG monitoring; however, embodiments of the invention are not limited to any particular number of leads.

Analog front end section 110 may include a multiplexor 111 for selecting various signals from the set of leads 120, EMI (electromagnetic interference) and low pass filtering on each input, and delta-sigma analog-to-digital converters 112 that may include high pass filtering. Right leg drive (RLD) signal 113 may be derived from a selected combination of one or more of the input signals.

Standard monitoring typically needs signal frequencies between 0.05-30 Hz. Diagnostic monitoring needs frequencies from 0.05-1000 Hz. Some of the 50 Hz/60 Hz common mode interference can be cancelled with a high input-impedance instrumentation amplifier (INA), which removes the AC line noise common to both inputs. To further reject line power noise, the signal may be inverted and driven back into the patient through the right leg by an amplifier. Only a few micro amps or less are required to achieve significant CMR improvement and stay within the UL544 limit. In addition, 50/60 Hz digital notch filters may be used to reduce this interference further.

Analog section 110 may be implemented in a single integrated circuit, such as the ADS1294/6/8/4R/6R/8R which is a family of multichannel, simultaneous sampling, 24-bit, delta-sigma analog-to-digital converters (ADCs) with built-in programmable gain amplifiers (PGAs), internal reference, and an onboard oscillator. The ADS1294/6/8/4R/6R/8R incorporates all of the features that are commonly required in medical electrocardiogram (ECG) and electroencephalogram (EEG) applications. ADS129× devices are described in more detail in data sheet SBAS459I, revised January 2012, available from Texas Instruments, which is incorporated by reference herein.

When a low resolution (16 bit) ADC is used, the signal needs to be amplified significantly (typically 100×-200×) to achieve the necessary resolution. When a high resolution (24 bit) sigma delta ADC is used, the signal needs a modest gain, 0-5× for example. Hence a second gain stage and the circuitry needed to eliminate the DC offset may be removed. This leads to an overall reduction in area and cost. The delta sigma approach preserves the entire frequency content of the signal and gives abundant flexibility for digital post processing.

Signal processing section 140 is coupled to receive a stream of digital ECG data 150 from analog section 110. A digital signal processor (DSP) 141 is coupled to non-volatile memory 144 that may store instructions defining various signal processing algorithms. Random access memory (RAM) 143 may be used by DSP 141 for storage of data while performing the various signal processing algorithms. Display driver 142 may be a micro-control unit (MCU) that manages a graphical user interface (GUI) that is displayed on display device 145, which may be a liquid crystal screen (LCD), for example, or any other display device now known or later developed. DSP 141 and MCU 142 may be implemented in a single IC, such as an OMAP (Open Multimedia Application Platform) device available from Texas Instruments, for example. Other embodiments may use other implementations of processors or signal processors that are now known or later developed. For example, various types of system on a chip (SoC) ICs may contain two to sixteen, or more DSP cores, for example.

One or more wired interfaces 146 may be provided that support USB (Universal Serial Bus), RS232, or other types of wire interfaces for transferring processed ECG signals to another system for further evaluation. One or more wireless interfaces 147 may be provided that support ZigBee, Bluetooth, or other types of wireless interfaces for transferring processed ECG signals to another system for further evaluation. Furthermore, a wireless interface 147 may also be provided for sending processed ECG signals to a remote system via a cellular phone or data network, for example.

Power management logic 102, clock, temperature sensing logic and fan control logic may also be included in ECG system 100 to provide power and temperature control for analog system 110 and DSP system 140.

Note that most or all of the components included within signal processing section 140 may now be available within a mobile handset, such as a smart phone, that may be programmed to provide the needed signal processing. Previously, the cost of ECG, EMG, and EEG equipment was prohibitive for consumer type devices. Coupling an analog front end section 110 to a smart phone may provide a cost effective medical monitoring device when the smart phone is programmed to perform ECG processing, as will be described in more detail below.

Figure 2:
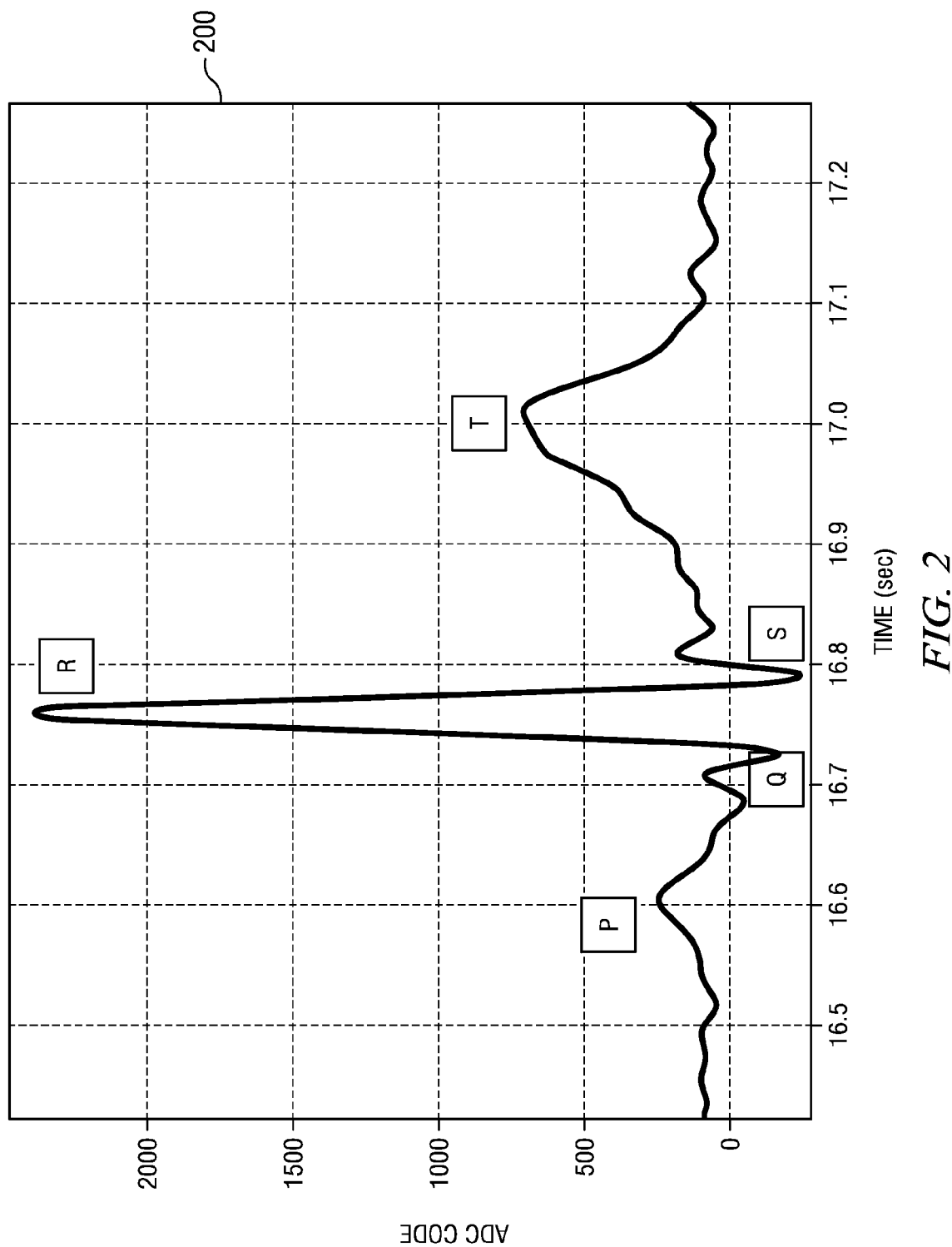
FIGS. 2-3 illustrate ECG plots that are analyzed by the mobile ECG system of FIG. 1.

FIG. 2 is a plot 200 illustrating a typical heart beat cycle. Like other biomedical signals, ECG is considered as a non stationary process. Its mean value and its standard deviation vary over the time. However, it contains useful information that can be interpreted as a pseudo deterministic pattern, referred to as a PQRST pattern. During each heartbeat a healthy heart will have an orderly progression of a wave of depolarization that is triggered by the cells in the sinoatrial node, spreads out through the atrium, passes through "intrinsic conduction pathways" and then spreads all over the ventricles. The normal ECG (EKG) is composed of a P wave, a QRS complex and a T wave. The P wave represents atrial depolarization and the QRS represents ventricular depolarization. The T wave reflects the phase of rapid repolarization of the ventricles.

Figure 3:
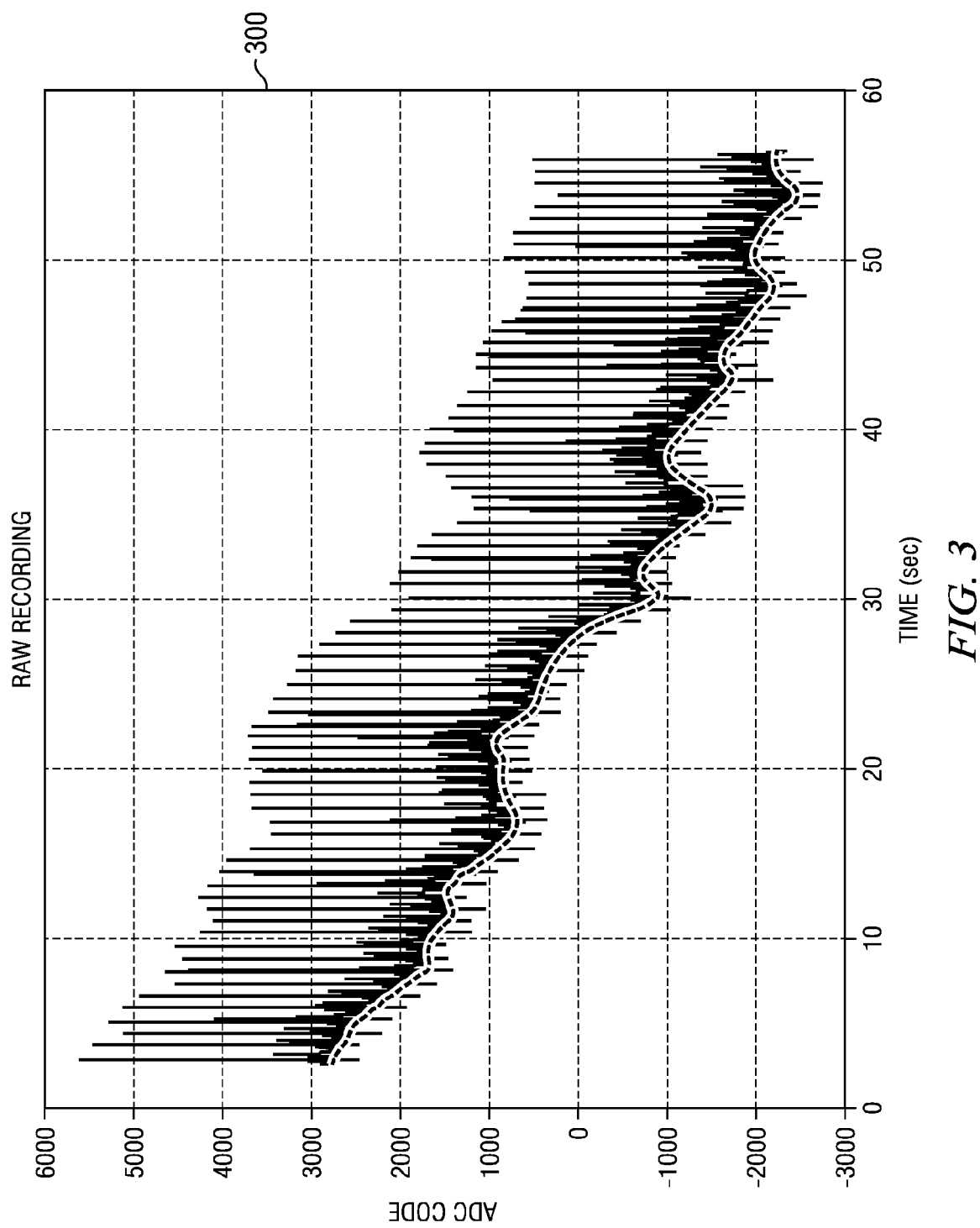

FIG. 3 is a plot 300 illustrating a sequence of raw ECG data 150 received from analog section 110, referring back to FIG. 1, over a period of about fifty seconds. In this embodiment, the analog-to-digital (ADC) code value is based on a 24 bit converter. Other embodiments may use different values based on different ADC converter precision. Noise, artifacts, EMG (electromyogram) interference from other muscles in the body, breathing, 60 Hz interference from power lines, etc may make simple analysis of ECG difficult. In order to preserve PQRST information, a bandwidth of approximately 3 Hz to 30 Hz may need to be provided. In some embodiments, a bandwidth up to approximately 1000 Hz may add accuracy.

Figure 4:
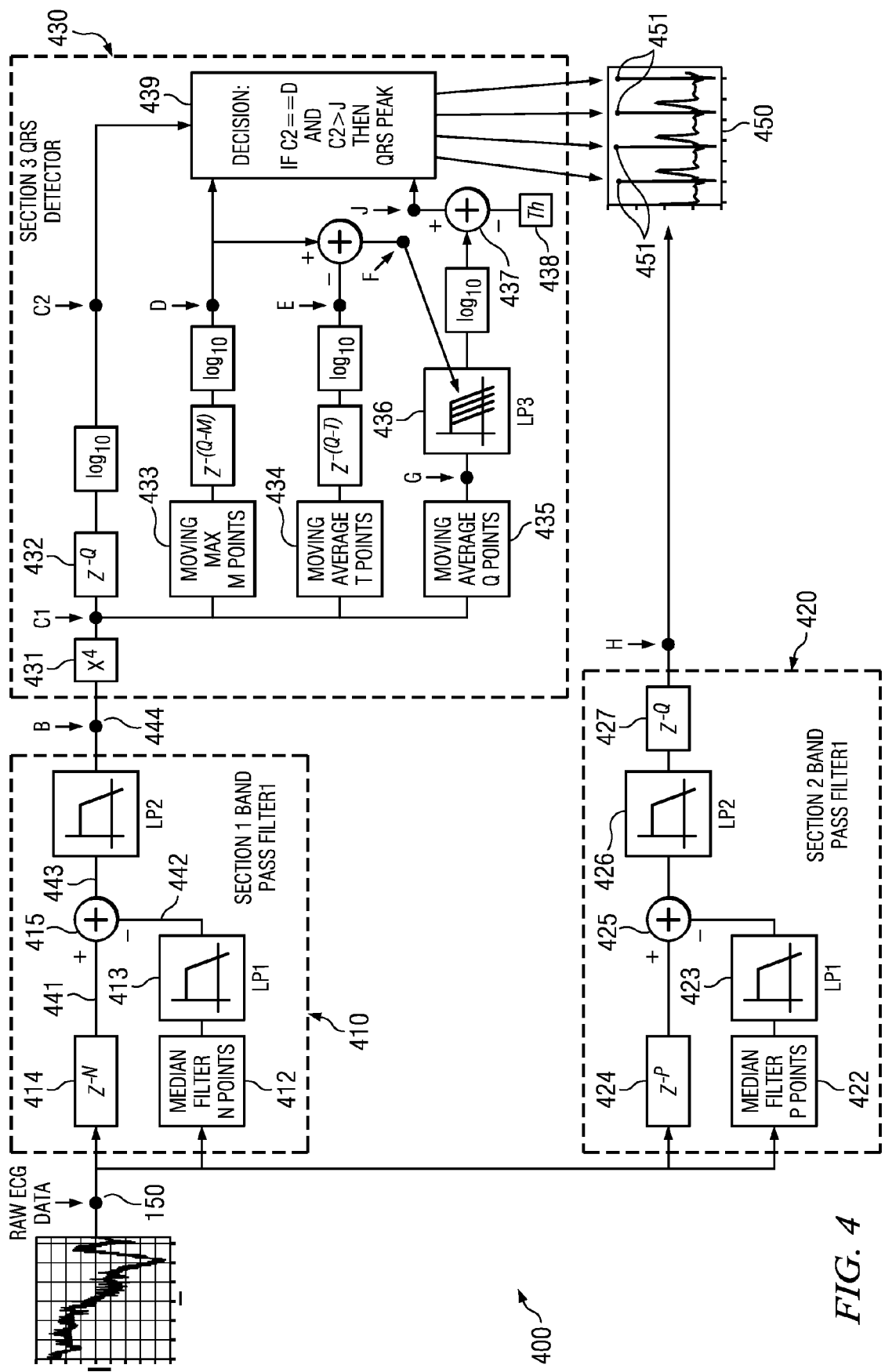
FIG. 4 is a schematic illustration of a real-time ECG filter implemented by the ECG system of FIG. 1.

FIG. 4 is a schematic illustration of a real-time ECG filter 400 implemented by the ECG system of FIG. 1. Robust detection of each QRS wave is important for further digital processing of an ECG sequence. A detector should work even when signal to noise ratio (SNR) is degraded. In this embodiment, the ECG filter is partitioned into three sections; section one 410 band pass filter, section two 420 band pass filter, and section three 430 QRS detector. A stream of raw ECG 150 is received from analog front end section 110, referring back to FIG. 1. Typically, it will include interference and distortion, as discussed with regard to FIG. 3. Embodiments of real-time ECG filters described herein were tested against the MIT-BIH database that includes 48 records, 30 minutes each, file based. This is a reference benchmark that is widely used for testing QRS detection algorithms. Embodiments described herein obtained 99.7% sensitivity and 99.9% positive predictability, similar to medical grade equipment using more complex non-real time algorithms.

Section two 420 is intended to provide a band-pass filtered ECG ready for cardiologist interpretation. In this embodiment, the raw data ECG is recorded by analog front-end 110 using a sampling frequency of 250 Hz. In another embodiment, a higher or a lower sampling frequency may be used. The ECG raw data is filtered in non linear manner using median filter (P points) 422 so that all high frequency components are removed and then conveyed through low pass filter LP1 423 in order to remove the remaining median filter noise. The same ECG raw data is delayed 424 by P samples and the output of LP1 filter 423 is subtracted 425 from it so that baseline wander of the ECG is suppressed. This combination of median filter 422, LP1 filter 423, and subtraction 425 from the original delayed signal is equivalent to high pass filtering. Low pass filter LP2 426 is a 5th order filter that has a cut-off frequency of 33 Hz and produces a filtered ECG signal H that is delayed 427 in order to align with the results from section three 430. Output signal H is ready for cardiologist interpretation. An example of filtered ECG signal H is illustrated at 450. By using an appropriate value for P, the overall PQRST wave is preserved and not distorted. Typically, a value for P may be selected to be P=Fs/2, for example.

Section one 410 is intended to prepare the ECG signal for beat detector 430. It is identical to section two except median filter 412 is changed to have a point value of (N). By selecting an appropriate value for N, baseline wander, P wave, and T wave are also suppressed on this section; such that only a QRS portion of the signal is preserved for further processing as signal B 444. Typically, a value for N may be selected to be N=Fs/10, for example.

Section three 430 represents the QRS detector itself. In order to amplify the high frequency content of a QRS wave, signal B is squared twice 431 to produce signal C1. From signal C1 three threshold signals are derived as follows. Signal C1 is scaled non-linearly to form signal C2. Each sample k of the signal C2 is produced as a logarithm on base 10, delayed 432 by Q samples, as indicated by equation (1).

$$C2_k = \log 10(C1_k) \quad (1)$$

A first threshold signal is signal D. Each sample k of the signal D is produced using a moving maximum 433 using M points sliding window on the signal C1, taken as a logarithm on base 10 and delayed by Q-M samples, as indicated by equation (2). Thus, signal D represents peak values of signal C1.

$$D_k = \log 10(\max(C_1(k) \ldots C_1(k+M))) \quad (2)$$

A second threshold signal is signal E. Each sample k of the signal E is produced using a moving average 434 using T points sliding window on the signal C1, taken as logarithm on base 10 and delayed by Q-T samples as indicated by equation (3). Thus, signal E represents average values of signal C1 over the window range.

$$E_k = \log 10 \left( \frac{\left( \sum_{m=0}^{m=M-1} C_1(k+m) \right)}{M} \right) \quad (3)$$

A third threshold signal is signal G. Each k sample of the signal G is obtained using a moving max using Q points sliding window on the signal C1 as indicated by equation (4).

$$G_k = (\max(C_1(k) \ldots C_1(k+Q))) \quad (4)$$

Signal G is passed through a filter LP3 436 having a transfer function according to equation (5).

$$H(z) = \frac{b_0 + b_1 \cdot z^{-1}}{1 + a_1 \cdot z^{-1}} \quad (5)$$

where, the coefficients a1, b0, b1 are dynamically calculated as a function of difference between the signal D and the signal E according to equation (6).

$$F_k = s \cdot (D_k - E_k) \quad (6)$$

where s is a scaling constant. Coefficients a0, a1, b0, and b1 are then obtained from a quasi-linear regression.

The a1, b0, b1 were calculated (iteratively for Fc=[1-10 Hz]) using known methods available in environments such as Matlab, Octave, etc. For instance, the function [B,A]=BUTTER(N,Wn), returns b0 and b1 and a0 in [B,A] vectors by using in input N=order and Wn=2*pi*Fc/Sampling freq. The algorithm behind this is:

Choose the cut-off frequency Fc and filter order (Fc=[1-10 Hz] and order is 1);

For each pair of Fc and order derive the corresponding analog transfer function;

Use bilinear transform applied to get the corresponding digital coefficients.

In this embodiment, the variations of b0, b1, and a1 versus cutoff frequency Fc are quasilinear and can be written: b0=b1=0.034*Fc+0.064; a1=0.022*Fc+0.99. The cutoff frequency value Fc=[1-10 Hz] may be substituted in the equations for every sample with Fk from equation (6) by appropriate scaling. For example, a value of Fk=0 translates into Fc=1 Hz and 100 dB value of Fk corresponds to 10 Hz Fc.

A third threshold signal J is formed from the output of the filter H(z) 436 expressed in dB shifted down 437 by threshold 438, which in this example is selected to be: threshold=6 dB. As explained above, signal Fk is proportional to the difference between Dk and Ek, therefore proportional to the ratio (difference in dB) between the peak and the average of the signal C1. When the ECG signal is noisy, the Peak to Average Ratio is low, therefore the cutoff frequency of H (z) is low, and the J signal (which is the main threshold) is strongly low-pass filtered in order to avoid false detections. When signal C1 is clean, the cut-off frequency of LP3 increases and the J signal is less low pass filtered and therefore can follow the low values of C1 signal. This avoids missing beats (false negative). Each decision of beat detector 439 is performed using the signal C2, D and J. If C2==J and C2>D then the QRS peak is considered as a true beat (where "==" means C2 is equal to J). It is worth noting that C2 is equal to J only on a single point 451 for each beat. Therefore, the beats may now be annotated on signal H that is provided as the output of section two 420.

An example signal H is illustrated at 450 with annotated heartbeats indicated at 451. The annotation may be provided along with signal 450 for use by a cardiologist while interpreting filtered ECG signal 450.

Figure 5:
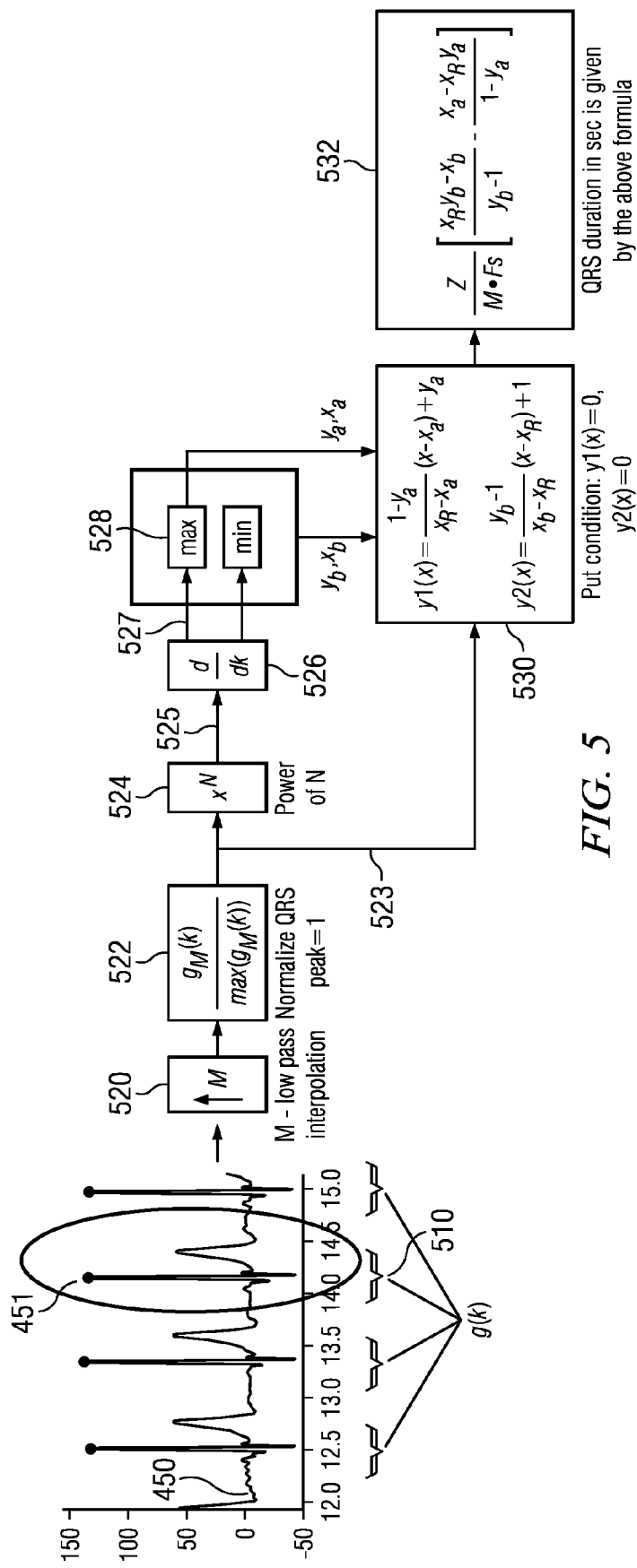
FIG. 5 is diagram illustrating a process for determining QRS duration.

Heart rate may be computed as follows as indicated by equation (7).

$$HR = \frac{60 \cdot B_{nb}}{T} = \frac{60 \cdot B_{nb} \cdot F_s}{N} \text{ [beats/minute]} \quad (7)$$

where:
$B_{nb}$ is the number of detected beats
$F_s$ is sampling frequency
N is number of acquired samples
T is the observation window, seconds FIG. 5 is diagram illustrating a process for determining QRS duration by selecting a portion of samples from the filtered ECG data surrounding the R point; and deriving QRS duration of the PQRST pattern by processing only the selected portion of samples.

A stream of raw ECG data samples comprising PQRST pattern cycles is received from a set of leads, such as ECG data 150, referring again to FIG. 4. Baseline wander is minimized by filtering the raw ECG data to form filtered ECG data. In this embodiment, filtering the raw ECG data may be performed as described with regard to FIG. 4 to form normalized signal 450. In another embodiment, filtering of the raw ECG data may be performed using another known or later developed technique.

A portion of the signal is extracted 510 around the QRS peak; this portion is referred to as g(k). The sampling frequency at this stage is Fs. The size of the extracted portion 510 may be based on the overall duration of a PQRST pattern and the normal QRS duration, which is typically 80-120 msec. For example, a window of 300 msec is more than enough to determine QRS duration for any human heart rate or QRS shape. When the heart rate is known, a bit more elaborate window around R may be dynamically selected in order to reduce computation and power dissipation; for example, a window may be selected using equation (8), or a similar equation.

$$QRS \text{ window} = 60/HR*0.4 + 0.2 \quad (8)$$

Functional stage 520 performs a low pass interpolation of g(k) by a factor M, to produce signal gM(k) 523. A typical value for M is 32 for a sampling frequency Fs=~250 Hz, which produces signal gM(k) that has an effective sampling frequency of 8000 Hz. The index corresponding to the R peak of gM(k) is xR, which corresponds to the sample indicated at 451.

Signal gM(k) is then normalized in stage 522 so that max normalized gM(k) is equal to one. The max gM(k) also corresponds to the R peak.

The normalized gM(k) signal 523 is then processed with a non-linear function in stage 524 to form a reduced noise signal 525 from the normalized gM(k) portion of samples. In this embodiment, the non-linear function is a power of N which causes all values <<1 to get much lower. This effectively increases the signal to noise ratio and therefore increases immunity to the noise. In this embodiment, N=4; however in other embodiments N may be selected to be larger or smaller. In a system in which noise has been eliminated by other means, N may be selected to be N=1.

The first derivative of the reduced noise signal is then taken in stage 526 to form signal 527. A maximum point and a minimum point of the derivative signal is then computed in stage 528 in order to find the rising and falling inflexion point indexes (xa, xb) and corresponding amplitudes (ya, yb) on the normalized gM(k) curve.

Two straight line equations are then formed in stage 530 using the rising inflection index and corresponding gM(k) curve amplitude (xa, ya) and the falling inflection point index and corresponding gM(k) curve amplitude (xb, yb) together with the R peak xr, as illustrated by equations (9) and (10).

$$y1(x) = \frac{1 - y_a}{x_R - x_a}(x - x_a) + y_a \quad (9)$$

-continued $$y2(x) = \frac{y_b - 1}{x_b - x_R}(x - x_R) + 1 \quad (10)$$

Equations (9) and (10) are then solved to determine the values of x when y1(k)=0 and y2(k)=0, which define to points where the two straight lines cross the base line. The QRS duration may now be computed in stage 532 as a function of xR, xa, xb, ya, yb, M and Fs as shown equation (11).

$$QRS \text{ duration[msec]} = \frac{Z}{M \cdot Fs}\left[\frac{x_R y_b - x_b}{y_b - 1} - \frac{x_a - x_R y_a}{1 - y_a}\right] \quad (11)$$

Scaling factor Z is a constant that is related to the non-linear power function N. In this embodiment, for N=4, Z=1.06. Z was determined experimentally for this embodiment by measuring the QRS duration on a variety of QRS patterns. The only dependence is the factor N, since the higher the value of N, the thinner the gM(k)^N reduced noise sequence. In another embodiment that uses a different technique to collect and filter the raw ECG data, or a different interpolation filter, for example, a different scaling factor Z may need to be determined.

Figure 6:
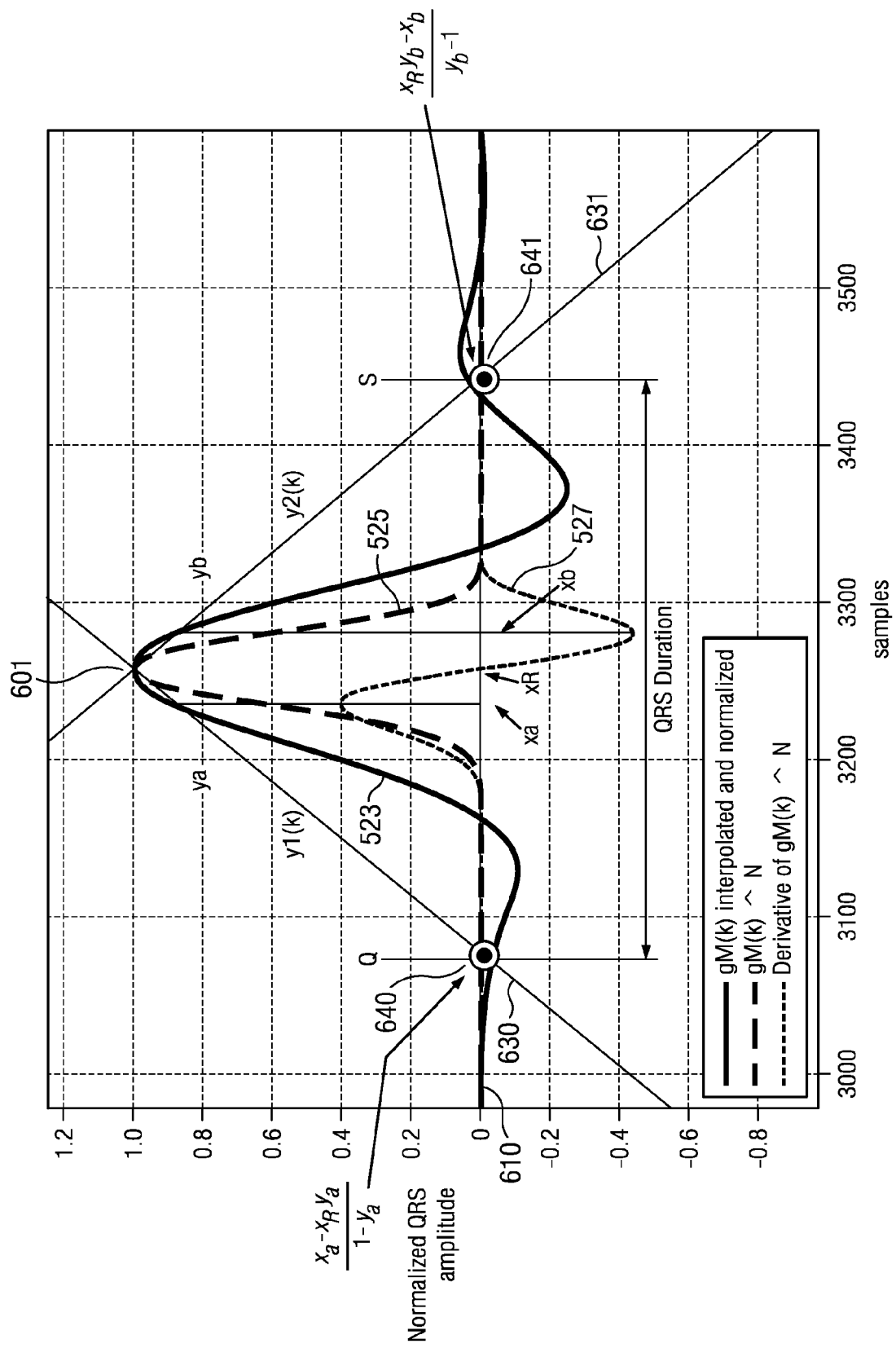
FIG. 6 is a plot illustrating a graphical representation of the process of FIG. 5.

FIG. 6 is a plot illustrating a graphical representation of the process illustrated in FIG. 5. Normalized gM(k) signal 523, reduced noise signal 525, and derivative signal 527 are illustrated. Base line 610 represents amplitude=0 for the normalized gM(k) signal 523.

Point 601 represents the max gM(k), which also corresponds to the R peak indicated at 451 in FIG. 5. The maximum value of derivative signal 527 defines index xa, which is then projected to amplitude ya on gM(k) curve 523. Similarly, the minimum value of derivative signal 527 defines index xb, which is then projected to amplitude yb on gM(k) curve 523. Straight line equation 630 is then constructed to cross (xa, ya) and max point 601. Straight line equation 631 is constructed to cross (xb, yb) and max point 601. Straight line 630 crosses base line 610 at point 640, as determined by equation 609. Straight line 631 crosses base line 610 at point 641 as determined by equation 10. The difference in time between point 641 and point 640, as determined by equation 611, correlates closely with the QRS duration for the QRS cycle, as illustrated by the Q and S points. As shown in equation (11), a scaling factor Z may be used to adjust the difference between points Q and S to improve the accuracy of the derived QES duration, as described above.

Figure 7:
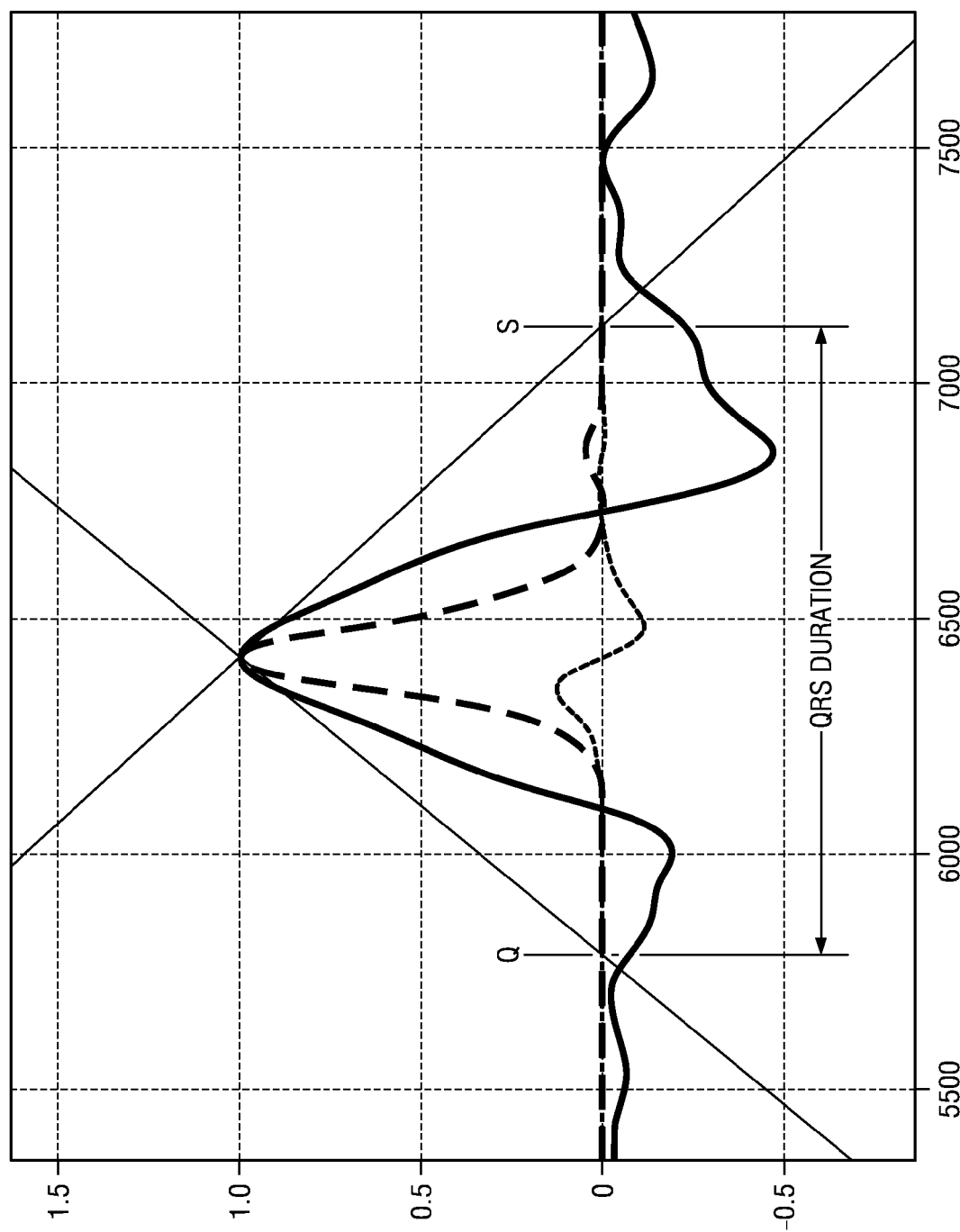
FIGS. 7-8 illustrate QRS duration results on pathological QRS shapes.
Figure 8:
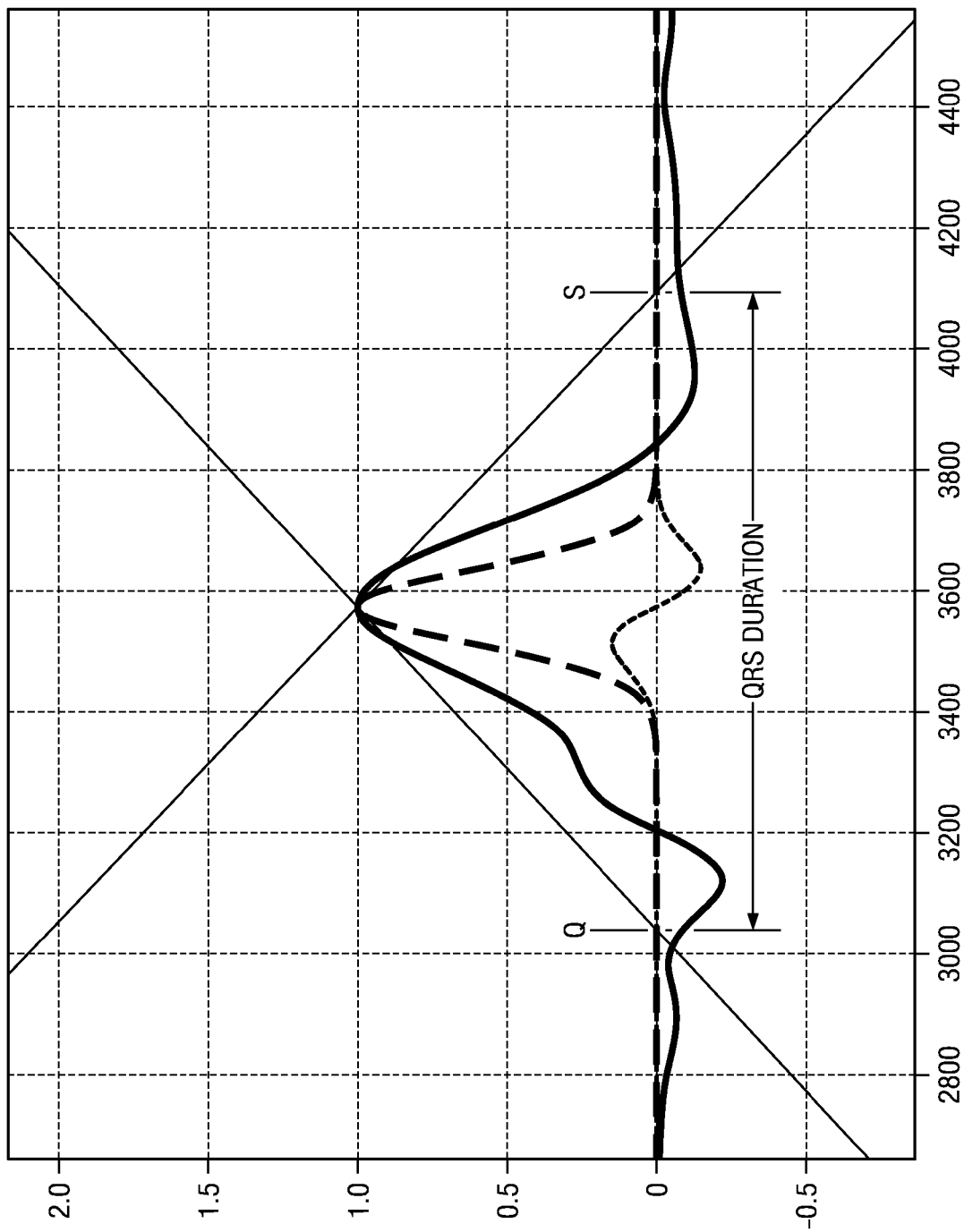

FIGS. 7-8 illustrate QRS duration results on pathological QRS shapes. The algorithm was validated using various types of QRS shapes to verify the algorithm works very well for unusual (pathological) QRS shapes. FIG. 7 is a QRS pattern extracted from record 108 of the MIT-BIH database (real ECG data) that includes a large ST depletion region, while FIG. 8 is a QRS pattern extracted from record 109 of the MIT-BIH database.

Figure 9:
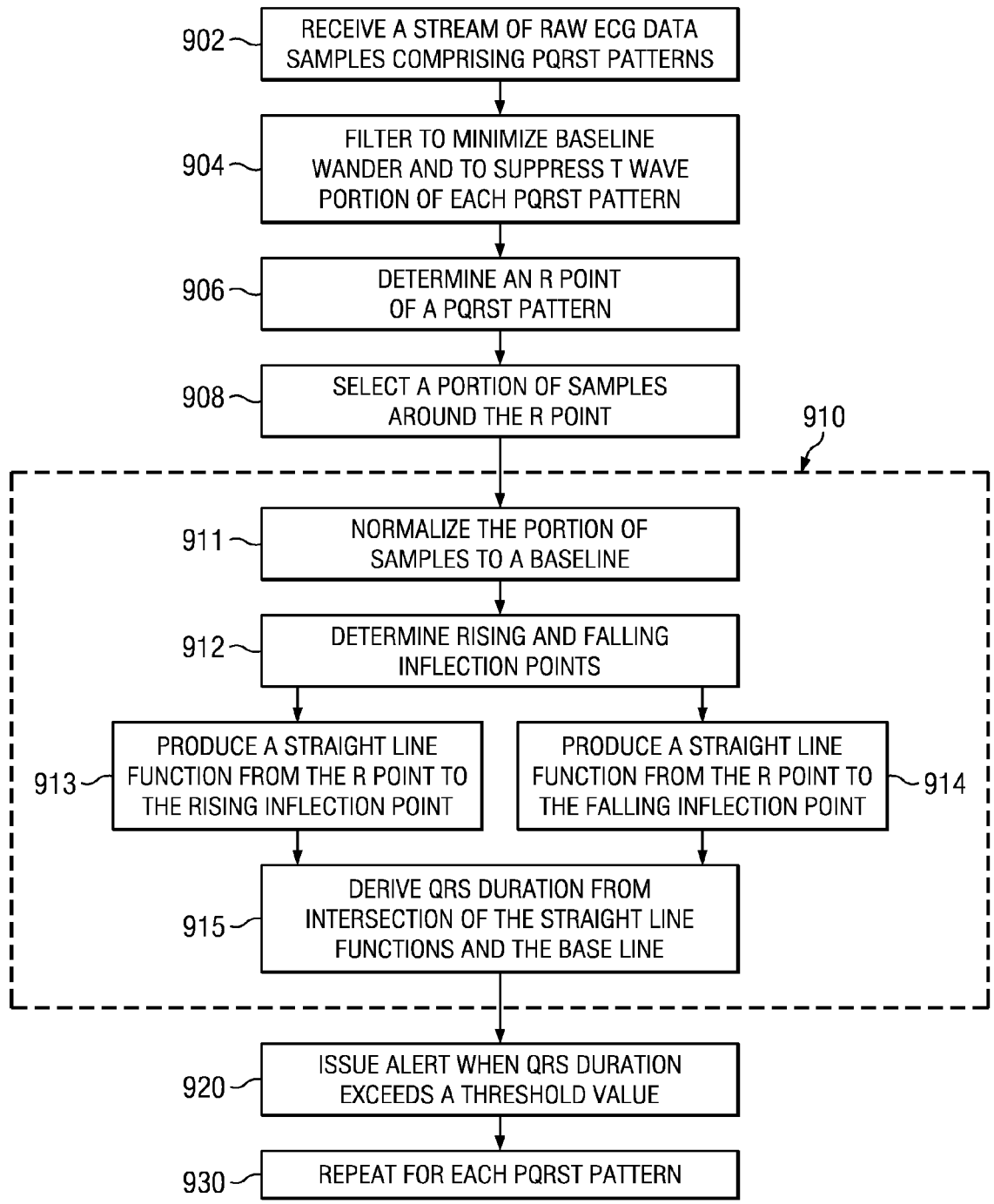
FIG. 9 is a flow chart illustrating operation of ECG analysis by the ECG system.

FIG. 9 is a flow chart illustrating operation of ECG analysis by the ECG system. Embodiments may be implemented on a mobile handset device, such as a smart phone or personal digital assistant, for example. A stream of raw ECG data samples is received 902 from an analog front end subsystem that samples and converts ECG signals into a stream of ECG data samples, as described in more detail above. The stream of ECG data samples represents a periodic sequence of PQRST patterns.

The raw ECG data is filtered 904 to form filtered ECG data by using a non-linear filter to minimize baseline wander and to suppress a T wave portion of each PQRST pattern. Filtering 904 of the raw ECG data may be done by filtering the raw ECG data using a cascade of median filter and low pass filter, delaying the raw ECG data, and subtracting an output signal of the low pass filter from the delayed raw ECG data in order to deliver a high pass filtered data, for example, as described in more detail above.

An R point of a PQRST pattern in the filtered ECG data is determined 906. This may be done as described above in more detail with regard to R points 451, for example. The R point is the maximum sample point of the filtered PQRST pattern.

A portion of samples is selected 908 from the filtered ECG data surrounding the R point. As described above, the size of the selected portion may be based on the overall duration of a PQRST pattern and the normal QRS duration, which is typically 80-120 msec. For example, a window of 300 msec is more than enough to determine QRS duration for any human heart rate or QRS shape. When the heart rate is known, a bit more elaborate window around R may be dynamically selected in order to reduce computation and power dissipation; for example, a window may be selected using equation (8), or a similar equation.

QRS duration of the PQRST pattern is determined 910 by processing the selected portion of samples. This may be done by normalizing 911 the portion of samples to the baseline, determining 912 a rising inflection point and a falling inflection point by taking a first derivative of the normalized portion of samples, producing 913 a straight line function from the R point (which is the maximum sample of the normalized portion of samples) and the rising inflection point, and producing 914 a straight line function from the R point and the falling inflection point.

The QRS duration may then be derived 915 from a difference in time between an intersection of the base line and the first straight line function and an intersection of the base line and the second straight line function.

A non-linear function may be applied to the normalized 911 portion of samples prior to determining the rising and falling inflection points to form a reduced noise portion of samples. As described above in more detail, the non-linear function may be a simple power of N which causes all values <<1 to get much lower. This effectively increases the signal to noise ratio and therefore increases immunity to the noise. In this embodiment, N=4; however in other embodiments N may be selected to be larger or smaller. In a system in which noise has been eliminated by other means, N may be selected to be N=1, in which case application of the non-linear function is not needed.

The rising and falling inflection points may be projected from the reduced noise portion of samples onto the normalized portion of samples for producing the straight line functions. When a non-linear function has not been applied to the reduced noise samples, then the inflection points may be determined using the reduced noise samples directly.

Normalization 911 may also include performing an M factor interpolation of the portion of samples prior to normalizing the portion of samples to improve signal fidelity of the sampled ECG data. Factor M may be selected based on the sampling frequency of the ECG data. A typical value for M is 32 for a sampling frequency Fs=~250 Hz, which produces signal gM(k) that has an effective sampling frequency of 8000 Hz.

Derivation 915 of the QRS duration may include scaling the QRS duration by a scale factor Z, wherein Z is a function of N, as described in more detail above.

When the QRS duration exceeds a threshold value, an alert may be provided 920 to a user of the mobile device. This may be in the form of a message on the screen of the device, a warning sound, vibration, etc. The threshold value may be set or selected by the user via a user interface provided by the mobile device, for example. A default threshold value may also be selected. A default value of 120 ms may be provided, for example.

This process may then be repeated 930 for each PQRST pattern. The duration of each PQRST pattern is determined individually, so that there is no loss of duration accuracy due to averaging or other types of post processing.

Figure 10:
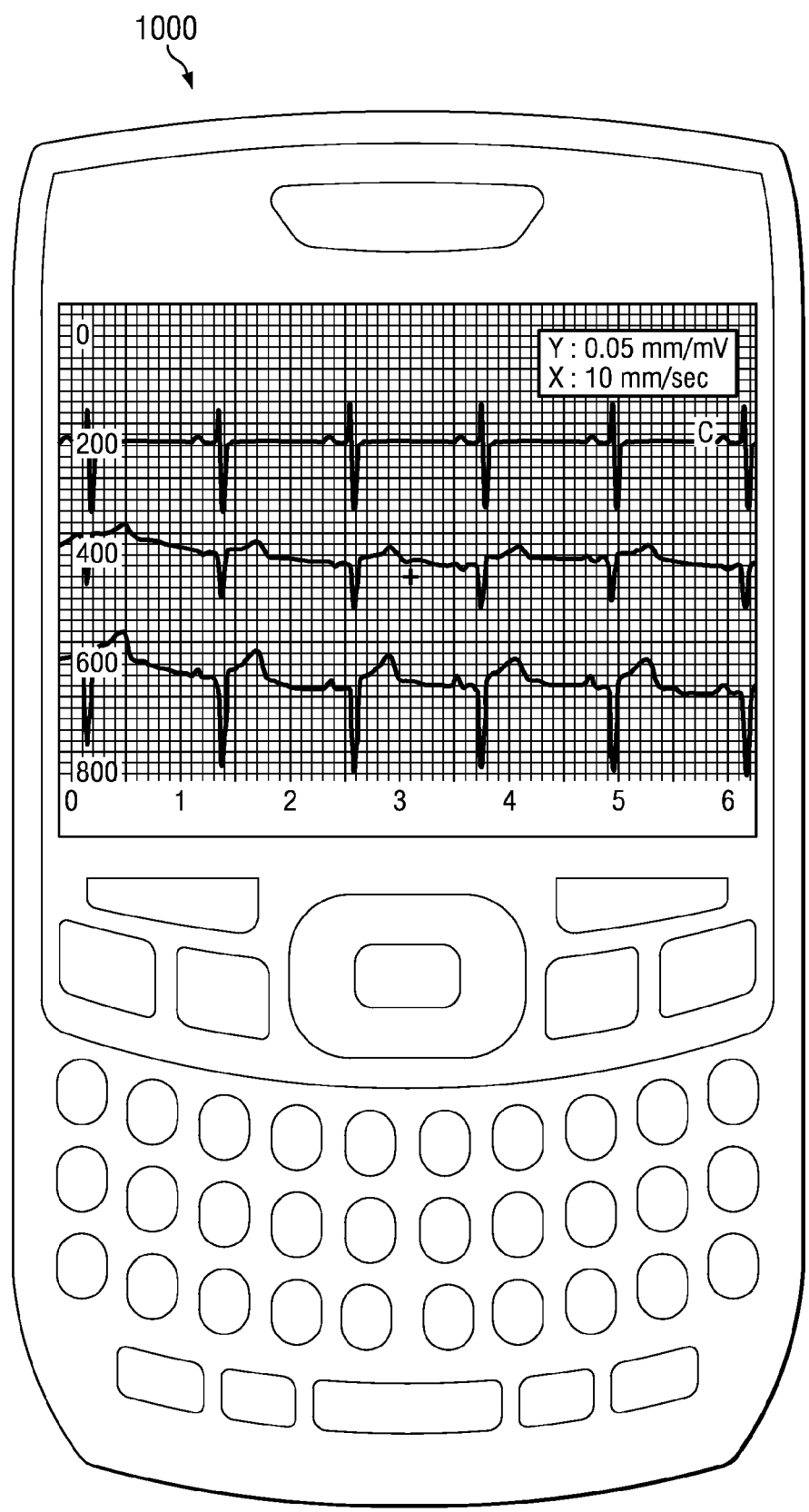
FIG. 10 illustrates an ECG being displayed on a mobile consumer device.

FIG. 10 illustrates an ECG being displayed on a mobile consumer device 1000. In this example, three ECG signals are being displayed, on for each lead of a three lead set-up. Using the keypad and a user interface provided by mobile device 1000, a user may select or specify an alert point for QRS duration. Software executed on mobile device 1000 will then process each PQRST pattern in the ECG data and inform the user and/or send an alert to a remote receiver, such as at a doctor's office or to another fixed or mobile device that may provide the alert indicator to a friend or family member, for example.

Figure 11:
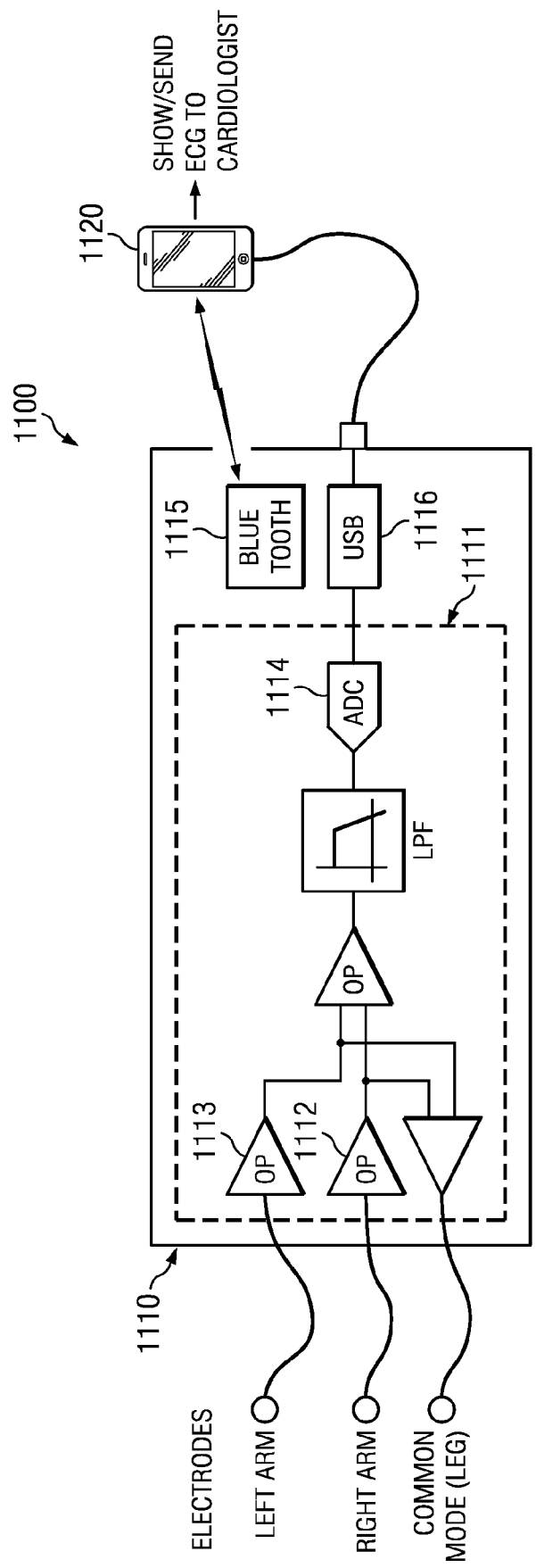
FIG. 11 illustrates another embodiment of a mobile ECG system that utilizes a mobile handset.

FIG. 11 illustrates another embodiment of a mobile ECG system 1100 that utilizes a mobile handset 1120. Analog front end module 1110 may include high-impedance inputs for the various electrode leads, such as op-amps 1112, 1113. Analog to digital converter 1114 converts low pass filtered analog signals to digital representations. In this embodiment, ADC 1114 has a precision of 24 bits. In other embodiments, ADC with greater or lesser precision may be used. Three electrode leads are illustrated in this example, which is useful for sports and simple monitoring uses. Other embodiments may include more electrode leads, as discussed in more detail above.

Analog section 1111 may be implemented in a single integrated circuit, such as the ADS1294/6/8/4R/6R/8R which is a family of multichannel, simultaneous sampling, 24-bit, delta-sigma analog-to-digital converters (ADCs) with built-in programmable gain amplifiers (PGAs), internal reference, and an onboard oscillator. The ADS1294/6/8/4R/6R/8R incorporates all of the features that are commonly required in medical electrocardiogram (ECG) and electroencephalogram (EEG) applications.

USB function 1116 may transmit the digital sequence of ECG samples produced by ADC to a USB input on mobile phone 1120. Alternatively, a Blue Tooth transmitter circuit 1115 may be included to wirelessly transmit the digital sequence of ECG samples produced by ADC to a Blue Tooth receiver on mobile phone 1120.

Mobile phone 1120 is representative of any of several smart phones that are available from a variety of vendors. A smart phone typically includes signal processing hardware and capabilities that are similar to signal processing section 140 of FIG. 1. Application software, also referred to as an "app," may be downloaded into the phone using the normal app download process for that smart phone. The app is configured to perform the filtering, thresholding, and QRS detection functions and QRS duration function that are described in more detail above by executing software instructions stored in memory that is accessible by a DSP processor, or other type of processor, that is included within smart phone 1120. As described in more detail above, the application may monitor the processed ECG signal and provide heart beat information, along with detecting various alert conditions, such as QRS duration, HRV, bigeminy, and large ST segment depletion, for example.

The electrodes may be connected to a subject, such as a person or animal, to monitor the performance of the subject's heart in real-time. The ECG app may display an ECG signal on a display screen of the smart phone, for example. The ECG app may display ECG pre-alerts on the display screen, or sound an audible alert using a speaker that is included within the smart phone, for example. The ECG app may also forward the filtered ECG signal, equivalent to signal H on FIG. 4, in real-time to a remote monitoring system using the data transmission capabilities that are included within the smart phone, for example. The ECG app may also forward pre-alert conditions that it has detected to the remote monitoring system.

The remote monitoring system may be located in a hospital or in a doctor's office, for example. A cardiologist may immediately review the ECG signal and associated pre-alert information on the remote monitoring system. The cardiologist may interact with the subject using the voice channel of the smart phone while ECG data continues to be transmitted to the remote site using a data channel of the smart phone.

Figure 12:
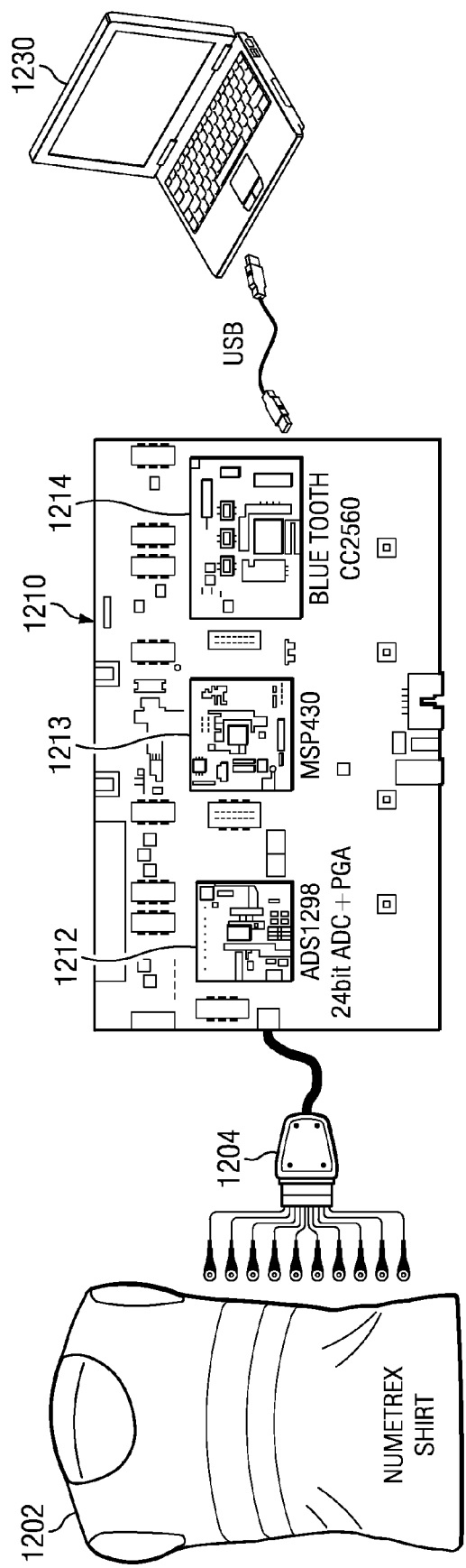
FIGS. 12-13 illustrate other embodiments of a mobile ECG system.

FIG. 12 illustrates another embodiment of a mobile ECG system. In this example, analog front end module 1210 may be coupled to a set of leads 1204 that are in turn coupled to termination points on a shirt 1202 that includes electrodes that are affixed to the shirt and arranged to make skin contact with a subject when shirt 1202 is worn by the subject. An example of shirt 1202 is a NuMetrex shirt or sports bra, available from Textronics.

Front end module 1210 is similar to front end module 1110, and may be implemented to support twelve ECG leads, for example, or a fewer number of ECG leads. Front end module may be implemented using an ADS1294 analog to digital converter 1212, as described in more detail above. A microcontroller may be coupled to ADC 1212 and control data transmission from ADC 1212 to a USB output. The microcontroller may also be coupled to a blue tooth circuit 1214 and thereby control wireless transmission of data from ADC 1212. Microcontroller 1213 may be a MSP430 device, available from Texas Instruments, for example. Blue tooth circuit 1214 may be a CC2560 device, available from Texas Instruments, for example.

A USB cable may be used to couple front end module 1210 to a laptop 1230, for example. Laptop 1230 is representative of any number of known portable computers that include sufficient processing power to perform the real-time filtering and QRS identification described in more detail above. Laptop 1230 is configured to receive a stream of ECG data from front end module 1210. Laptop 1230 is also configured with a software application that makes use of the processor included within laptop 1230 to process a stream of ECG data transmitted from a subject that is wearing shirt 1202.

The app is configured to perform the filtering, thresholding, QRT detection, and QRS duration functions that are described in more detail above by executing software instructions stored in memory that is accessible by a DSP processor that is included within computer 1230. As described in more detail above, the application may monitor the processed ECG signal and provide heart beat information, along with detecting various pre-alert conditions, such as QRS duration, HRV, bigeminy, and large ST segment depletion, for example.

The electrodes may be connected to a subject, such as a person or animal, to monitor the performance of the subject's heart in real-time. The ECG app may display an ECG signal on a display screen of laptop computer 1230, for example. The ECG app may display ECG pre-alerts on the display screen, or sound an audible alert using a speaker that is included within the laptop computer, for example. The ECG app may also forward the filtered ECG signal, equivalent to signal H on FIG. 4, in real-time to a remote monitoring system using the data transmission capabilities that are included within the laptop computer, for example. The ECG app may also forward alert conditions that it has detected to the remote monitoring system. Transmission to the remote monitoring site may be done via the internet, for example, used a wired or wireless connection included within laptop computer 1230.

The remote monitoring system may be located in a hospital or in a doctor's office, for example. A cardiologist may immediately review the ECG signal and associated alert information on the remote monitoring system. The cardiologist may interact with the subject using the voice channel on the laptop computer, such as voice over internet, while ECG data continues to be transmitted to the remote site using a data channel of the laptop computer.

Figure 13:
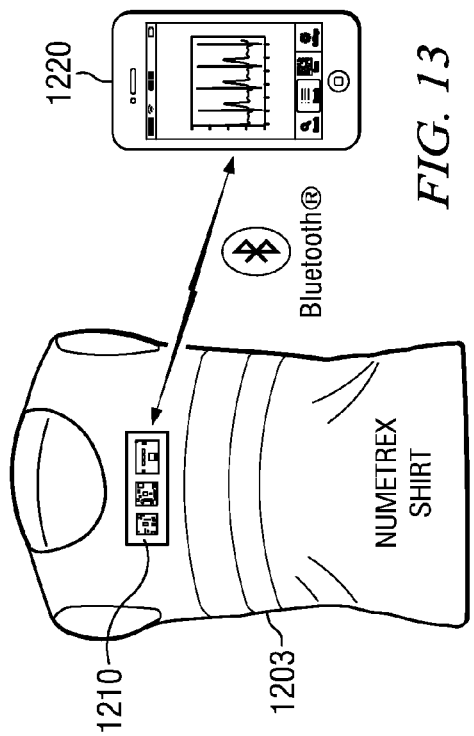

FIG. 13 illustrates another embodiment of a mobile ECG system. In this example, analog front end module 1210 is attached to shirt 1203 and be coupled to a set of termination points on shirt 1203 that includes electrodes that are affixed to the shirt and arranged to make skin contact with a subject when shirt 1203 is worn by the subject. An example of shirt 1203 is a NuMetrex shirt or sports bra that is suitably modified to carry analog front end module 1210.

Analog front end module 1210 is configured to wirelessly transmit ECG data collected from a subject that is wearing shirt 1203 to a nearby blue tooth receiver located in smart phone 1220, for example. Smart phone 1220 is configured with an ECG app, as described in more detail above, and may thereby process and display the ECG data in real time and also transmit the ECG data to a remote site for analysis by a cardiologist or other health care giver.

Thus, a low cost, mobile system has been described that provides real time QRS detection performance that is better than published existing research. There is no need for any learning phase as is required by many prior algorithms. Various embodiments may provide additional heart information beyond the just heart rate by analyzing PQRST waveforms; this may allow various embodiments to provide real-time pre-alerts for various conditions. These low cost, mobile systems may be useful for home use, fitness use, etc.

Other Embodiments

While the invention has been described with reference to illustrative embodiments, this description is not intended to be construed in a limiting sense. Various other embodiments of the invention will be apparent to persons skilled in the art upon reference to this description. For example, the analog front end section may be packaged in various manners now known or later developed that will provide protection and ease of use. For example, the package may be waterproof and rugged so that the analog front end may be permanently attached to a shirt or sports bra and survive normal use and cleaning processes.

The analog front end may be battery powered, or it may be packaged with an energy scavenging unit that derives power from motion of the test subject, solar energy, etc.

While a wired USB link or a wireless blue tooth link have been described, other embodiments may use any sort of known or later developed wired (metallic or optical) or wireless interconnect protocol that supports the necessary transfer rate to support real-time transmission of filtered ECG data. Of course, the necessary transfer rate will depend on the ADC precision and sample rate selected for the embodiment.

While a personal computer and a smart phone were described herein for providing the requisite signal processing to perform the filtering and detection functions, other types of mobile consumer devices may be used to implement the filtering and detection functions described herein, such as a tablet computer, a personal digital assistant, etc. In general, as used herein, a consumer device is a general purpose device that may be used by a consumer for other tasks in additional to providing ECG monitoring.

While the embodiments described herein performed QRS duration within a mobile device, in another embodiment QRS duration may be performed by a system located at a remote site using ECG data transmitted from a mobile system, for example.

While logarithmic scaling of the thresholds was described herein, another embodiment may use another form of non-linear scaling. Another embodiment may use linear representations and use ratios instead of differences for comparing threshold values.

In other embodiments, the requisite signal processing to perform the filtering and detection functions may be provided by a digital processing system designed explicitly for ECG use, by a non-mobile system, a medical grade system, etc.

While the systems described herein may be capable of transmitting filtered ECG data to a remote site in real time, other embodiments may provide a storage function to store a portion of filtered ECG data for later transfer to a remote system.

Embodiments of the filters and methods described herein may be provided on any of several types of digital systems: digital signal processors (DSPs), general purpose programmable processors, application specific circuits, or systems on a chip (SoC) such as combinations of a DSP and a reduced instruction set (RISC) processor together with various specialized accelerators. An SoC may contain one or more mega-cells which each include custom designed functional circuits combined with pre-designed functional circuits provided by a design library.

The techniques described in this disclosure may be implemented in hardware, software, firmware, or any combination thereof. If implemented in software, the software may be executed in one or more processors, such as a microprocessor, application specific integrated circuit (ASIC), field programmable gate array (FPGA), or digital signal processor (DSP). The software that executes the techniques may be initially stored in a computer-readable medium such as compact disc (CD), a diskette, a tape, a file, memory, or any other computer readable storage device and loaded and executed in the processor. In some cases, the software may also be sold in a computer program product, which includes the computer-readable medium and packaging materials for the computer-readable medium. In some cases, the software instructions may be distributed via removable computer readable media (e.g., floppy disk, optical disk, flash memory, USB key), via a transmission path from computer readable media on another digital system, etc.

Certain terms are used throughout the description and the claims to refer to particular system components. As one skilled in the art will appreciate, components in digital systems may be referred to by different names and/or may be combined in ways not shown herein without departing from the described functionality. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" and derivatives thereof are intended to mean an indirect, direct, optical, and/or wireless electrical connection. Thus, if a first device couples to a second device, that connection may be through a direct electrical connection, through an indirect electrical connection via other devices and connections, through an optical electrical connection, and/or through a wireless electrical connection.

Although method steps may be presented and described herein in a sequential fashion, one or more of the steps shown and described may be omitted, repeated, performed concurrently, and/or performed in a different order than the order shown in the figures and/or described herein. Accordingly, embodiments of the invention should not be considered limited to the specific ordering of steps shown in the figures and/or described herein.

It is therefore contemplated that the appended claims will cover any such modifications of the embodiments as fall within the true scope and spirit of the invention.

What is claimed is:

1. A system comprising:
    an analog front end module configured to collect ECG data from one or more leads and operable to convert the analog ECG data to digital ECG data; and
    a mobile device coupled to receive the digital ECG data;
    wherein the analog front end is operable to:
        receive a stream of raw ECG data samples comprising PQRST pattern cycles; and
        filter the raw ECG data to form filtered ECG data to minimize baseline wander; and
    wherein the mobile device is configured to:
        determine an R point of a PQRST pattern in the filtered ECG data;
        select a portion of samples from the filtered ECG data surrounding the R point;
        normalize the portion of samples to a baseline;
        determine a rising inflection point and a falling inflection point by taking a first derivative of the normalized portion of samples;
        produce a first straight line function from a maximum one of the normalized portion of samples and the rising inflection point;
        produce a second straight line function from the maximum one of the normalized portion of samples and the falling inflection point; and
        derive the QRS duration from a difference in time between an intersection of the baseline and the first straight line function and an intersection of the base line and the second straight line function.

2. The system of claim 1, the mobile device further configured to:
    apply a non-linear function to the normalized portion of samples prior to determining the rising and falling inflection points to form a reduced noise portion of samples; and
    project the rising and falling inflection points from the reduced noise portion of samples onto the normalized portion of samples for producing the first and second straight line functions.

3. The system of claim 2, wherein the non-linear function is $x^N$ for each sample x of the normalized portion of samples; and
    wherein the mobile device is further configured to scale the QRS duration by a scale factor Z, wherein Z is a function of N.

4. The system of claim 1, wherein the mobile device is further configured to perform an M factor interpolation of the portion of samples prior to normalizing the portion of samples.

5. The system of claim 1, wherein selecting a portion of samples comprises selecting a sequence of samples around the R point over a time period that is less than half of the cycle time of the PSRST pattern cycle.

6. The system of claim 1, further comprising providing an alert via a user interface on the mobile device when the QRS duration exceeds a threshold value.

7. The system of claim 1, wherein the mobile device is a smart phone.

* * * * *